United States Patent

Moshchitsky et al.

[11] Patent Number: 5,360,850
[45] Date of Patent: Nov. 1, 1994

[54] ASYMMETRICAL BENZOTRIAZOLYLPHENOLS

[75] Inventors: Semyon Moshchitsky, Old Bride, N.J.; William E. Leistner, Atlantic Beach, N.Y.

[73] Assignee: Fairmount Chemical Company, Inc., Newark, N.J.

[21] Appl. No.: 159,376

[22] Filed: Nov. 30, 1993

Related U.S. Application Data

[62] Division of Ser. No. 58,012, May 5, 1993, Pat. No. 5,292,890.

[51] Int. Cl.$^5$ .................................................. C08K 5/34
[52] U.S. Cl. ............................................. 524/91; 524/94
[58] Field of Search .................................... 524/91, 94

[56] References Cited

U.S. PATENT DOCUMENTS 5,001,177  3/1991  Winfried et al. ................ 524/91
5,110,849  5/1992  Karasawa et al. ................ 524/91

*Primary Examiner*—Kriellion S. Morgan
*Attorney, Agent, or Firm*—Richard S. Roberts

[57] ABSTRACT

Provided are asymmetrical, ultraviolet stabilizers which are hydroxyphenyl benzotriazolylphenol compounds of the formula:

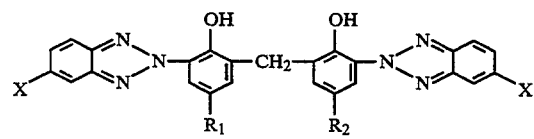

wherein:
- $R_1$ is $C_1$ to $C_{18}$ alkyl, $C_6$ to $C_{10}$ aryl, $C_7$ to $C_{16}$ arylalkyl, $C_1$ to $C_{12}$ alkoxy, $C_6$ to $C_{10}$ aryloxy, $C_7$ to $C_{16}$ arylalkoxy, cyclopentyl, cyclohexyl or cumyl;
- $R_2$ is $C_1$ to $C_{18}$ alkyl, $C_6$ to $C_{10}$ aryl, $C_7$ to $C_{16}$ arylalkyl, $C_1$ to $C_{12}$ alkoxy, $C_6$ to $C_{10}$ aryloxy, $C_7$ to $C_{16}$ arylalkoxy, cyclopentyl, cyclohexyl or cumyl;
- $R_1$ is different from $R_2$; and
- X is selected from the group consisting of hydrogen, halogen, $C_1$ to $C_{12}$ alkyl, and $C_1$ to $C_{12}$ alkoxy. The invention also pertains to a process for their preparation and stabilized polymer blends containing the stabilizers.

11 Claims, No Drawings

ASYMMETRICAL BENZOTRIAZOLYLPHENOLS

This is a divisional of co-pending application Ser. No. 08/058,012 filed on May 5,1993 U.S. Pat. No. 5,292,890.

BACKGROUND OF THE INVENTION

The present invention pertains to ultraviolet light stabilizers for plastics and coating compositions, or more particularly, to novel types of compounds which are asymmetrical benzotriazolylphenols.

It is well known in the art that plastics are unstable over time upon exposure to ultraviolet light. Such plastics undergo a decrease in mechanical strength and an increase in unwanted color when exposed to uv radiation. It is also known to improve the resistance of plastics and coating compositions to deterioration by the addition of a uv light absorber. Such commonly used stabilizers include compounds of the hydroxyphenyl benzotriazole family, including hydroxyphenyl benzotriazole monomers and dimers. Hydroxyphenyl benzotriazole monomers are well known in the art and are disclosed in earlier U.S. Pat. Nos. 3,204,896; 3,189,6515; 5,097,041; 4,943,637 and 5,104,992. Hydroxyphenyl benzotriazole dimers are also known.

The benzotriazole dimers have an advantage over the monomeric benzotriazole u.v. absorbers. The dimers have higher molecular weight which makes them much less volatile. This is very important considering the high temperatures required for the processing of engineering plastics. In addition, these dimers possess high thermal stability so they are not decomposed when exposed to elevated temperatures for prolonged periods of time.

Benzotriazole type u.v. absorbers, including dimers, function through a mechanism involving the phenolic hydrogen and the nitrogens of the triazole ring. In attempts to reduce the volatility of benzotriazole monomers, various organic groups were added to the phenolic ring and/or halogens to the benzene ring of the benzotriazole. Volatility was usually reduced by substitution of one or two organic groups on the phenolic ring. While these measures did improve the volatility problem, it also reduced the total u.v. absorption capability of the benzotriazole monomers. Most commercial benzotriazoles which are available today are disubstituted.

U.S. Pat. Nos. 4,684,679, and 4,812,498 disclose the symmetrical dimers 2,2'-methylene-bis-(4-hydrocarbyl-6 benzotriazolylphenols). U.S. Pat. Nos. 4,684,679 and 4,937,348 disclose a process for preparing the symmetrical dimers 2,2'-methylene-bis-(4-hydrocarbyl-6-benzotriazolylphenols) by first forming the Mannich base of a described benzotriazole monomer and then reacting the Mannich base with the same benzotriazole monomer or the same Mannich base. All of the above patents are incorporated herein by reference. Indeed, a common feature of all known benzotriazole dimers is that they are symmetrical, that is, all units of the dimer or polymer contain the same single hydroxyphenyl benzotriazole monomer unit. For example, U.S. hydroxyphenyl benzotriazole monomer unit. For example, U.S. Pat. No. 4,937,348 shows a hydroxyphenyl benzotriazole dimer having the formula:

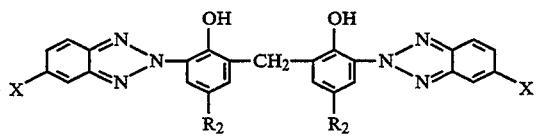

These compounds are symmetrical because each R$_2$, which is an alkyl group having 1–18 carbon atoms at the 4 position of each of the phenolics, is identical. To synthesize benzotriazole dimers, one is limited to benzotriazole compounds where there is but a single substitution on the phenolic ring. Disubstitution on the phenolic ring prevents the formation of a dimer through a Mannich base or by any known reaction. This fact limits the number of benzotriazole dimers to the few monosubstituted benzotriazoles commercially available.

This is disadvantageous because the physical properties of symmetrical dimers of hydroxyphenyl benzotriazoles have limited properties with regard to melting point, molecular weight, uv absorption distribution, particle migration, and polymer compatibility. Since there are so few compounds in this dimer group, it is often impossible to select a symmetrical hydroxyphenyl benzotriazole having the best combination of properties. For example, while it may be desired for a melting point, it may not be compatible with the plastic of choice. It has now been unexpectedly found, that by independently varying the alkyl (hydrocarbyl) group at the 4-position of the phenolic ring so that each half of the dimer has a different substitution, numerous dimers can now be synthesized. The melting point, molecular weight, and uv absorption distribution properties can be tailored to the requirements for the polymer of choice. It has been found that each dimer half contributes its beneficial characteristics. Also unexpectedly, the melting points of the asymmetrical dimers are lower than one would normally expect. This allows the asymmetrical dimers to be used with polymers which are processed at lower temperatures and the lower melting point allows easier dispersion in polymers.

It has also been unexpectedly found that in general, asymmetrical dimers display higher solubility in organic non-polar solvents than symmetrical dimers made from the same monomers, as shown in Table 1 below. The symmetrical dimers usually have limited solubility in polar and non-polar solvents and have higher melting points. With better solubility and lower melting point, asymmetrical benzotriazoles are more easily and more uniformly blended in the plastic to be stabilized. The asymmetrical benzotriazoles make it possible to synthesize many different combinations of monomers to form dimers with tailor made characteristics.

SUMMARY OF THE INVENTION

The invention provides an asymmetrical hydroxyphenyl benzotriazolylphenol compound having the formula:

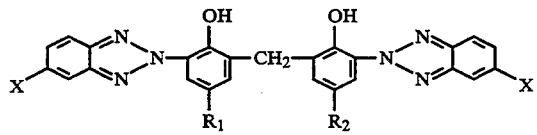

wherein:

$R_1$ is $C_1$ to $C_{18}$ alkyl, $C_6$ to $C_{10}$ aryl, $C_7$ to $C_{16}$ arylalkyl, $C_1$ to $C_{12}$ alkoxy, $C_6$ to $C_{10}$ aryloxy, $C_7$ to $C_{16}$ arylalkoxy, cyclopentyl, cyclohexyl or cumyl; $R_2$ is $C_1$ to $C_{18}$ alkyl, $C_6$ to $C_{10}$ aryl, $C_7$ to $C_{16}$ arylalkyl, $C_1$ to $C_{12}$ alkoxy, $C_6$ to $C_{10}$ aryloxy, $C_7$ to $C_{16}$ arylalkoxy, cyclopentyl, cyclohexyl or cumyl;

$R_1$ is different from $R_2$; and

X is selected from the group consisting of hydrogen, halogen, $C_1$ to $C_{12}$ alkyl, and $C_1$ to $C_{12}$ alkoxy.

The invention also provides a stabilized polymer composition which comprises a polymeric compound such as polycarbonates and their copolymers, polyacrylates and their copolymers, polyacetals, polystyrenes, polyacrylonitrile, polydienes, polyesters, polyamides, polyurethanes, acrylonitrile-butadiene-styrene resins, polyphenylene sulfides, fluorinated polymers, polyolefins, acrylonitrile polymers and copolymers, vinyl polymers and copolymers, vinylidene polymers and copolymers, polyvinylacetate and its copolymers, and cellulosic polymers, and from about 0.1% to about 5% based on the weight of the polymeric composition of the above asymmetrical hydroxyphenyl benzotriazolylphenol.

The invention further provides a process for the preparation of asymmetrical hydroxyphenyl benzotriazolylphenols having the formula:

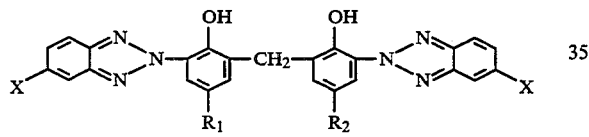

which comprises:

a.) reacting a 4-hydrocarbyl-6-benzotriazolylphenol having the formula:

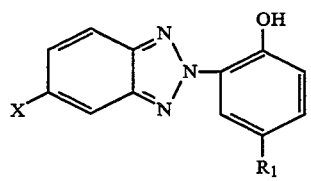

with an amine having the formula $HNR_3R_4$ and formaldehyde in an organic solvent to produce a Mannich base having the formula:

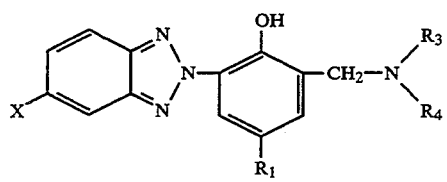

and b.) reacting the Mannich base with a 4-hydrocarbyl-6-benzotriazolylphenol having the formula

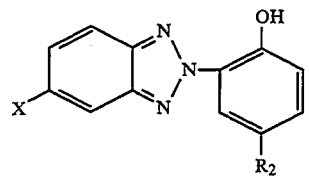

in the presence of an alkaline catalyst, wherein:

$R_1$ is $C_1$ to $C_{18}$ alkyl, $C_6$ to $C_{10}$ aryl, $C_7$ to $C_{16}$ arylalkyl, $C_1$ to $C_{12}$ alkoxy, $C_6$ to $C_{10}$ aryloxy, $C_7$ to $C_{16}$ arylalkoxy, cyclopentyl, cyclohexyl or cumyl;

$R_2$ is $C_1$ to $C_{18}$ alkyl, $C_6$ to $C_{10}$ aryl, $C_7$ to $C_{16}$ arylalkyl, $C_1$ to $C_{12}$ alkoxy, $C_6$ to $C_{10}$ aryloxy, $C_7$ to $C_{16}$ arylalkoxy, cyclopentyl, cyclohexyl or cumyl;

$R_1$ is different from $R_2$;

$R_3$ and $R_4$ are selected from the group consisting of hydrogen, $C_1$ to $C_6$ alkyl, and groups where $R_3$ and $R_4$ taken together form a X is selected from the group consisting of hydrogen, halogen, $C_1$ to $C_{12}$ alkyl, and $C_1$ to $C_{12}$ alkoxy.

DETAILED DESCRIPTION OF THE PREFERRED EMBODIMENT

In the practice of the present invention one begins with a hydroxyphenyl benzotriazole monomer of the formula

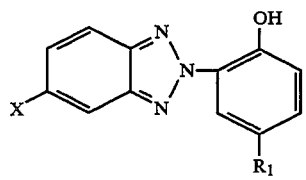

wherein $R_1$ is $C_1$ to $C_{18}$ alkyl, $C_6$ to $C_{10}$ aryl, $C_7$ to $C_{16}$ arylalkyl, $C_1$ to $C_{12}$ alkoxy, $C_6$ to $C_{10}$ aryloxy, $C_7$ to $C_{16}$ arylalkoxy, cyclopentyl, cyclohexyl or cumyl and X is selected from the group consisting of hydrogen, halogen, $C_1$ to $C_{12}$ alkyl, and $C_1$ to $C_{12}$ alkoxy. Benzotriazole monomers may be prepared by any method known in the art including those taught in U.S. Pat. Nos. 5,097,041, 4,943,637 and 5,104,992. 2-aryl-2H-benzotriazoles monomers may be produced by reducing o-nitroazobenzenes through a 2-phenylbenzotriazole-N-oxide intermediate. A wide variety of reduction techniques is known. Reduction of o-nitroazobenzenes to 2-phenylbenzotriazole by zinc in the presence of sodium hydroxide is disclosed in U.S. Pat. Nos. 3,018,269; 3,230,194; 3,773,751; 4,041,044; and 4,224,451. Reduction using aldehyde reducing agents and aromatic ketone catalysts is disclosed in U.S. Pat. No. 4,835,284. Reduction using saccharides and an aromatic ketone catalyst is disclosed in U.S. Pat. No. 4,780,541. All of these patents are incorporated herein by reference. These show methods for the preparation of benzotriazoles by reductive cyclization of azo dyes with saccharides in the presence of aromatic ketone catalysts, which act by receiving hydrogen from the reducing agent and giving hydrogen to a material to be reduced. In each of these cases, saccharide reduction is catalyzed by such aromatic ketone catalysts as substituted and unsubstituted fluorenone.

The asymmetrical dimers of the present invention may be prepared by a two step process including first forming the Mannich base of a hydroxyphenyl benzotriazole monomer, and then reacting the Mannich base with another hydroxyphenyl benzotriazole monomer except the pendent group from the phenyl ring is a different group than is present on the hydroxyphenyl benzotriazole used above to form the Mannich base. The Mannich base is prepared by reacting the first hydroxyphenyl benzotriazole with a dialkyl amine and formaldehyde in an organic solvent. The amines have the formula $HNR_3R_4$ and non-exclusively include secondary alkyl amines such as dimethylamine, diethylamine, di-n-propylamine, diisopropylamine, di-n-butylamine, di-t-butylamine, diisobutylamine, diamylamine, ethylmethylamine and ethylisopropylamine; and heteroalicyclic amines such as morpholine, piperidine and pyrrolidine. Formaldehyde or any of its polymeric forms can be used in the process of the invention such as gaseous formaldehyde, aqueous solutions of formaldehyde, paraformaldehyde, trioxane, trioxymethylene, tetraoxymethylene, and other solid polymers of formaldehyde.

Solvents useful for the process of the invention include essentially any inert organic solvent that is a solvent for the reactants. It is also contemplated that solvents may be such as alcohols, ethers, hydrocarbons and halocarbons, among others. These include alcohols such as methanol, ethanol, isopropanol, and n-butanol; hydrocarbons such as hexane, heptane, benzene, toluene, xylene, petroleum ethers, and mineral spirits, cycloaliphatic ethers such as furan, tetrahydrofuran and dioxane. The amount of solvent is not critical and can range from about 50 to about 500 weight percent based on the amount of hydroxyphenyl benzotriazole. The amounts of amine and formaldehyde in the reaction with the hydroxyphenyl benzotriazole in the solvent can be stoichiometric or slightly more and preferably each is in the range of from about 1.0 to about 2.0 mole or more per mole of 4-hydrocarbyl-6-benzotriazolylphenol. The Mannich base formation reaction can be carried out over a wide range of temperatures and is preferably from about 60° C. to about 150° C., or more preferably from about 90° C. to about 110° C. In the preferred embodiment, the reaction is preferably conducted for from about 10 hours to about 30 hours, or more preferably from about 20 hours to about 24 hours. The most advantageous reaction time may be determined by those skilled in the art.

The dimerization step is conducted by reacting the thusly produced Mannich base with a stoichiometric amount of a 4-hydrocarbyl-6-benzotriazolylphenol wherein the 4-hydrocarbyl group on the phenol is a $C_1$ to $C_{18}$ alkyl group but is different from the $C_1$ to $C_{18}$ alkyl group on the 4-hydrocarbyl-6-benzotriazolylphenol used to form the Mannich base. The dimerization reaction is preferably carried out in the presence alcoholates of an alkaline catalyst. Such include lower alkali metal alcoholates such as sodium methylate and sodium ethylate, alkali metal hydroxides such as sodium and potassium hydroxide, and alkali metal alkaline salts such as potassium carbonate and sodium carbonate. The amount of catalyst is not critical and preferably ranges from about 0.001 to about 50 parts by weight, or more preferably from about 0.01 to about 8 parts by weight per 100 parts of hydroxyphenyl benzotriazole. The reaction can be carried out over a wide range of temperatures and is preferably from about 120° C. to about 200° C., or more preferably from about 150° C. to about 170° C. In the preferred embodiment, the dimerization reaction is conducted for from about 2 hours to about 12 hours, or more preferably from about 3 hours to about 10 hours. The most advantageous reaction time may be determined by those skilled in the art.

As hereinbefore mentioned, it is known in the art that plastics are unstable over time upon exposure to ultraviolet light. Such plastics non-exclusively include polycarbonates and their copolymers, polyacrylates and their copolymers, polyacetals, polystyrenes, polyacrylonitrile, polydienes, polyesters, polyamides, polyurethanes, acrylonitrile-butadiene-styrene resins, fluorinated polymers, polyolefins, acrylonitrile polymers and copolymers, vinyl polymers and copolymers, vinylidene polymers and copolymers, polyvinylacetate and its copolymers, and cellulosic polymers, among others. The uv stability of such materials is improved by mixing the polymer with from about 0.1% to about 5% based on the weight of the polymer composition of the asymmetrical dimer of this invention. The composition may be formed by heating the polymer to its softening point in an extruder and adding the dimer to the melt to form a substantially uniform physical mixture. In the method of the invention, the polymer materials which are generally thermoplastics or cellulosic, and the dimer are blended in the desired quantities and heated to a temperature above the softening point of the polymer. The heating and blending can be done in either order, however, in the preferred embodiment, these processes are conducted simultaneously. The mixing may be conducted in any suitable equipment including a Banbury mixer, single or twin screw extruder, ribbon blender, injection molding machine, two roll mill or the like, thus forming a substantially uniform blend of the plastic material and the dimer. The mixing step is usually conducted for from about 0.1 minutes to about 10 minutes at temperatures mostly dependent on the softening point of the polymer being used. In the preferred embodiment, the heating is conducted at a temperature of from about 35° C. to about 350° C., or more preferably from about 100° C. to about 315° C., and most preferably from about 145° C. to about 300° C.

The asymmetrical hydroxyphenyl benzotriazoles of this invention can also be used as uv stabilizers for compositions such as organic coatings, and paints when blended along with such additional components as antioxidants, plasticizers, fillers, heat stabilizers, solvents, colorants and processing aids. The following non-limiting examples serve to illustrate the invention.

EXAMPLE 1

[2-Dipropylaminomethyl-4-(1,1,3,3-tetramethylbutyl)-6-(2H-benzotriazol-2-yl)]phenol I. 323g (1 Mole) of [4-(1,1,3,3-tetramethylbutyl)-6-(2H-benzotriazol-2-yl)]phenol and 257 g (1.2 mole) of bis(dipropylamino) methane are dissolved in 500 ml of butanol-1 and the mixture is heated at reflux for 24 hours. The solvent is vacuum distilled off and product crystallized from acetonitrile. Yield 414 g (95%). The melting point is 81.5° C.-83° C. and purity by HPLC is 99.8%.

II. 323 g (1 Mole) of [4-(1,1,3,3--tetramethylbutyl)-6-(2H-benzotriazol-2-yl)]phenol, 42 g (1.4 mole) of paraformaldehyde, and 303 g (3 mole) dipropylamine are dissolved in 500 ml of butanol-1 and the mixture heated at reflux for 20 hours. The solvent is vacuum distilled off and product crystallized from acetonitrile. Yield 98%. The melting point is 80° C.-82° C. and purity by HPLC is 99.5%.

III. 323 g (1 Mole) of [4-(1,1,3,3-tetramethylbutyl)-6-(2H-benzotriazol-2-yl)]phenol, 39 g (1.3 mole) of paraformaldehyde, and 303 g (3 mole) dipropylamine are heated with azeotropic removal of water and then the mixture is heated at 120° C.–125° C. for 20 hours. Dipropylamine is vacuum removed and the product crystallized from acetonitrile. Yield 396 grams (91%). The melting point is 81° C.–83° C. and purity by HPLC is 99.6%.

EXAMPLE 2

[2-Dimethylaminomethyl-4-methyl-6-(2H-benzotriazol-2-yl)]phenol

I. A mixture of 225 g (1 mole) of [4-methyl--6-(2H-benzotriazol-2-yl)]phenol, 248 g (2.2 mole) of 40% aqueous dimethylamine, 36 g (1.2 mole) of paraformaldehyde and 300 ml butanol-1 is heated at 85° C. to 90° C. with gentle reflux for 20 hours. The mixture is cooled to 10° C. The product is crystallized from acetonitrile to yield 211 g (75%). The melting point is 93° C.–97° C. and purity by HPLC is 99.2%.

II. A mixture of 225 g (1 mole) of [4-methyl-6-(2H-benzotriazol-2-yl)]phenol, 248 g (2.2 mole) of 40% aqueous dimethylamine, 36 g (1.2 mole) of paraformaldehyde and 300 ml isopropanol is heated in an autoclave at 120° C. and 50 psi pressure for 2 hours. The mixture is cooled to 10° C. The product is crystallized from acetonitrile to yield 87%. The melting point is 94° C.–96° C. and purity by HPLC is 99.4%.

EXAMPLE 3

[2,2'-Dihydroxy-3,3'-di-(2H-benzotriazol-2-yl)-5-(1,1,3,3-tetramethylbutyl)-5'-methyl]diphenylmethane I. 225 g (1 Mole) of 4-methyl-6-benzotriazol-2-yl-phenol, 20 g (0.5 mole) of sodium hydroxide and 800 ml of pseudocumene are dissolved at 90° C. to 95° C. and to this mixture is added 436 g (1 mole) of [2-dipropylaminomethyl-4-(1,1,3,3-tetramethylbutyl)-6-(2H-benzotriazol-2-yl)]phenol and the mixture is heated at 160° C. to 165° C. for 12 hours with constant distillation of water and dipropylamine. Half of the solvent is vacuum distilled, 100 g of acetic acid are added and the mixture is heated at 130° C. to 135° C. for 15 minutes. 900 g of methanol are added. The mixture is cooled to 10° C. and solid is filtered. Yield 532 g (95%). The melting point is 178° C.–185° C. (DMF) and purity by HPLC is 90%.

II. 323 g (1 Mole) of [4-(1,1,3,3-tetramethylbutyl)-6-(2H-benzotriazol-2-yl)]phenol, 31.5 g (1.05 mole) of paraformaldehyde, 260 g of dipropylamine and 500 ml of butanol-1 are heated at reflux for 24 hours. The solvent is vacuum distilled, 300 ml of pseudocumene are added and this mixture is added to a mixture of 4-methyl-6-benzotriazolylphenol 225 g (1 mole), sodium hydroxide 20 g (0.5 mole) and 500 ml of pseudocumene which has been preheated to 90° C.–95° C. The mixture is heated at 160° –165° C. for 12 hours with constant distillation of dipropylamine. Half of the solvent is vacuum distilled, 100 g of acetic acid are added and the mixture is heated at 130° C. to 135° C. for 15 minutes. 900 g of methanol are added. The mixture is cooled to 10° C. and solid is filtered. Yield 537 g (96%). The melting point is 177° C.–184° C. and purity by HPLC is 91%.

EXAMPLE 4

[2,2'-Dihydroxy-3,3'-di(2H-benzotriazol-2-yl)-5 methyl-5'-(1,1-dimethylethyl)]diphenylmethane 267 g (1 Mole) of [4-(1,1-dimethylethyl)-6-benzotriazol-2-yl]-phenol, 20 g (0.5 mole) of sodium hydroxide and 1000 ml of pseudocumene are dissolved at 150° C. to 155° C. with distillation of water. The mixture is cooled to 120° C. and to this mixture are added 282 g (1 mole) of [2-dimethylaminomethyl-4-methyl-6-(2H-benzotriazol-2-yl)]phenol and the mixture is heated at 165° C.–170° C. for 3 hours. During this time dimethylamine is eliminated from the reaction. Half of solvent is vacuum distilled, 100 g of acetic acid are added and the mixture is heated at 130° C.–135° C. for 15 minutes. 900 g of methanol are added. Yield 428 g (85%). The product is crystallized from methylcellosolve. The melting point is 216° C. to 219° C. Purity by HPLC is 96%.

EXAMPLE 5

[2,2'-Dihydroxy-3,3'-di-(2H-benzotriazol-2-yl)-5-(1,1-dimethylethyl)-5'-(1,1,3,3-tetramethylbutyl)]diphenylmethane 267 g (1 Mole) of 4-(1,1-dimethylethyl)-6-benzotriazol-2-yl-phenol, 20 g (0.5 mole) sodium hydroxide and 800 ml of pseudocumene are dissolved at 90° C. to 95° C. and to this mixture are added 436 g (1 mole) a [2-dipropylaminomethyl-4-(1,1,3,3-tetramethylbutyl)-6-(2H-benzotriazol -benzotriazol-2-yl)]phenol and the mixture is heated at 160° C. to 165° C. for 12 hours with constant distillation of water and dipropylamine. Half of solvent is vacuum distilled, 100 g of acetic acid was added and the mixture is heated at 130° C. to 135° C. for 15 minutes. 900 g of methanol are added. The mixture is cooled to 5° C. and oil is precipitated. Solvents are decanted, methyl cellosolve is added, the mixture is heated to reflux and filtered from some insolubles. Yield 271 g (38%), M.P. 220°–222° C. and purity by HPLC is 88%.

EXAMPLE 6 (COMPARATIVE)

Reaction of the Mixture of 4-methyl- and 4-t-octyl-6-benzotriazol-2-yl-phenols with Paraformaldehyde A mixture of 22.5 g (0.1 mole) of 4-methyl-6-benzotriazol-2-yl-phenol, 32.3 g (0.1 mole) of 4-t-octyl-benzotriazol-2-yl-phenol, 25 g of dipropylamine and 3 g (0.1 mole) of paraformaldehyde is heated at 140° C.–150° C. with azeotropic removal of $H_2O$ and dipropylamine. Then 60 g of pseudocumene and 0.9 g of NaOH are added and the mixture is heated at 160° C. for 10 hours. Half of the solvent is vacuum distilled. 20 g of acetic acid is added and the mixture heated at 130° C.–135° C. for 15 minutes and 200 g of methanol is added. An oily product is precipitated. According to HPLC, the oil contains a mixture of four products: symmetrical methyl derivatives—46%, symmetrical 4-octyl derivatives—24%, asymmetrical methyl-t-octyl derivatives—22% and 8% starting materials. This example shows that an attempt to form a dimer from 4-methyl-6-benzotriazol-2-yl-phenol and 4-t-octylbenzotrialzol-2-yl-phenol by direct condensation forms an undesirable mixture.

EXAMPLE 7

The following table compares the properties of two hydroxyphenyl benzotriazole monomers, their symmetrical dimers and an asymmetrical dimer of them. These data show that the asymmetrical dimer has a lower melting point than symmetrical dimer made from the same two starting monomers. The asymmetrical dimer is much more soluble in the non-polar solvent (pseudocumene) than either of the symmetrical dimer made from the same two starting monomers. The last two columns indicate that there is no significant difference in absorbance of uv light comparing the asymmetrical dimer to the symmetrical dimers made from the same two starting monomers.

TABLE 1

| COMPOUND | TYPE | MOLECULAR WEIGHT | MELTING POINT °C. | SOLUBILITY IN SOLVENTS (POLAR AND NON-POLAR) AT 25° C., IN GRAMS PER 100 GM. SOLVENT | | | |
|---|---|---|---|---|---|---|---|
| | | | | METHANOL (POLAR) (PROTONIC) | ACETONITRILE (POLAR) (APROTONIC) | DIMETHYL FORMAMIDE (POLAR) (APROTONIC) | PSEUDOCUMENE (NON-POLAR) |
| 2-(2'H-Benzotriazol-2'-yl)-4-methylphenol | Monomer | 225 | 128–132 | 0.1 | 0.8 | 5.8 | 6.0 |
| 2-(2'H-Benzotriazol-2'-4-t-octylphenol | Monomer | 323 | 103–104 | 0.5 | 0.8 | 10.2 | 55.1 |
| 2,2'-Methylene-Bis-[6-(2H-benzotriazol-2-yl)-4-methylphenol] | Symmetrical Dimer | 463 | 280–285 | insoluble | insoluble | 0.1 | 0.1 |
| 2,2'-Methylene-Bis-[6-(2H-benzotriazol-2-yl)-4-t-Octylphenol) | Symmetrical Dimer | 658 | 194–196 | 1.2 | 1.0 | 1.7 | 3.9 |
| [2,2'-dihydroxy-3,3'-di-(2H-benzotriazol-2-yl)-5-t-octyl-5'methyl] diphenylmethane | Asymmetrical Dimer | 560 | 178–185 | 0.1 | 0.1 | 0.5 | 9.0 |

| COMPOUND | ABSORBANCE AT GAMMA MAX. AT SET CONCENTRATION CHLOROFORM | |
|---|---|---|
| | 0.02 MMOL/1000 ML | 0.03 MMOL/1000 ML |
| 2-(2'H-Benzotriazol-2'-yl)-4-methylphenol | 1.445 (340 nm) | 0.484 (340 nm) |
| | 1.249 (300 nm) | 0.413 (300 nm) |
| 2-(2'H-Benzotriazol-2'-4-t-octylphenol | 1.012 (340 nm) | 0.480 (340 nm) |
| | 0.857 (300 nm) | 0.439 (300 nm) |
| 2,2'-Methylene-Bis-[6-(2H-benzotriazol-2-yl)-4-methylphenol] | 1.429 (350 nm) | 0.966 (350 nm) |
| | 1.355 (305 nm) | 0.912 (350 nm) |
| 2,2'-Methylene-Bis-[6-(2H-benzotriazol-2-yl)-4-t-Octylphenol) | 0.976 (350 nm) | 0.963 (350 nm) |
| | 0.969 (305 nm) | 0.956 (305 nm) |
| [2,2'-dihydroxy-3,3'-di-(2H-benzotriazol-2-yl)-5-t-octyl-5'methyl] diphenylmethane | 1.155 (350 nm) | 0.947 (350 nm) |
| | 1.116 (305 nm) | 0.922 (305 nm) |

What is claimed is:

1. A stabilized polymer composition which comprises a polymeric compound and from about 0.1% to about 5% based on the weight of the polymeric composition of an asymmetrical hydroxyphenyl benzotriazolylphenol compound having the formula:

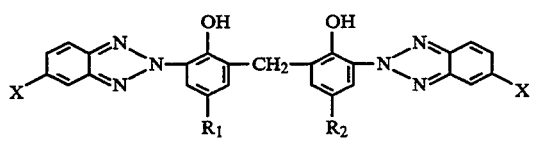

wherein:

$R_1$ is $C_1$ to $C_{18}$ alkyl, $C_6$ to $C_{10}$ aryl, $C_7$ to $C_{16}$ arylalkyl, $C_1$ to $C_{12}$ alkoxy, $C_6$ to $C_{10}$ aryloxy, $C_7$ to $C_{16}$ arylalkoxy, cyclopentyl, cyclohexyl or cumyl;

$R_2$ is $C_1$ to $C_{18}$ alkyl, $C_6$ to $C_{10}$ aryl, $C_7$ to $C_{16}$ arylalkyl, $C_1$ to $C_{12}$ alkoxy, $C_6$ to $C_{10}$ aryloxy, $C_7$ to $C_{16}$ arylalkoxy, cyclopentyl, cyclohexyl or cumyl;

$R_1$ is different from $R_2$; and

X is selected from the group consisting of hydrogen, halogen, $C_1$ to $C_{12}$ alkyl, and $C_1$ to $C_{12}$ alkoxy.

2. The stabilized polymer composition of claim 1 wherein the polymeric compound is selected from the group consisting of polycarbonates and their copolymers, polyacrylates and their copolymers, polyacetals, polystyrenes, polyacrylonitrile, polydienes, polyesters, polyamides, polyurethanes, acrylonitrile-butadiene-styrene resins, polyphenylene sulfide, fluorinated polymers, polyolefins, acrylonitrile polymers and copolymers, vinyl polymers and copolymers, vinylidene polymers and copolymers, polyvinylacetate and its copolymers, and cellulosic polymers.

3. The composition of claim 1 wherein X is hydrogen, $R_1$ is methyl and $R_2$ is t-octyl.

4. The composition of claim 1 wherein X is hydrogen, $R_1$ is methyl and $R_2$ is t-butyl.

5. The composition of claim 1 wherein X is hydrogen, $R_1$ is t-octyl and $R_2$ is t-butyl.

6. The composition of claim 1 wherein the polymeric compound is selected from the group consisting of polycarbonates and their copolymers.

7. The composition of claim 1 further comprising one or more components selected from the group consisting of as antioxidants, plasticizers, fillers, heat stabilizers, solvents, colorants and processing aids.

8. The composition of claim 2 wherein X is hydrogen, $R_1$ is methyl and $R_2$ is t-octyl.

9. The composition of claim 2 wherein X is hydrogen, $R_1$ is methyl and $R_2$ is t-butyl.

10. The composition of claim 2 wherein X is hydrogen, $R_1$ is t-octyl and $R_2$ is t-butyl.

11. The composition of claim 6 further comprising one or more components selected from the group consisting of as antioxidants, plasticizers, fillers, heat stabilizers, solvents, colorants and processing aids.

* * * * *